United States Patent [19]

Tanaka et al.

[11] Patent Number: 5,057,145

[45] Date of Patent: Oct. 15, 1991

[54] PHENYLALKYLIMIDAZOLE COMPOUNDS AS FUNGICIDES

[75] Inventors: Kenichi Tanaka; Shinji Nishimura; Hiroshi Kawada; Katsuya Yamaguchi; Yumi Tazaki; Yumi Mizumura; Chieko Nomura, all of Tokyo, Japan

[73] Assignee: Hodogaya Chemical Co., Ltd., Tokyo, Japan

[21] Appl. No.: 555,618

[22] Filed: Jul. 23, 1990

[30] Foreign Application Priority Data

Jul. 28, 1989 [JP] Japan .................... 1-193847

[51] Int. Cl.$^5$ ............... C07D 233/54; A01N 43/48; A01N 43/64

[52] U.S. Cl. ....................... 71/92; 548/335; 514/396

[58] Field of Search ............ 548/341, 335; 71/92; 514/396

[56] References Cited

FOREIGN PATENT DOCUMENTS

| 62-187403 | 8/1987 | Japan | 548/341 |
|---|---|---|---|
| 63-35564 | 2/1988 | Japan | 548/341 |
| 63-154668 | 6/1988 | Japan | 548/341 |

Primary Examiner—Mary C. Lee
Assistant Examiner—Robert C. Whittenbaugh
Attorney, Agent, or Firm—Oblon, Spivak, McClelland, Maier & Neustadt

[57] ABSTRACT

A substituted phenylalkylimidazole compound of the formula:

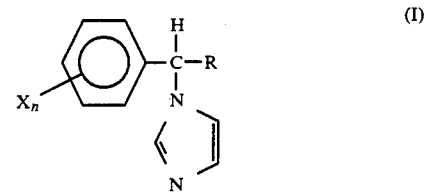

wherein R is an alkyl group or an alkenyl group, X is a halogen atom, a methyl group, a methoxy group, a phenoxy group, a trifluoromethyl group or a dimethylamino group, and n is an integer of 1 or 2.

3 Claims, No Drawings

PHENYLALKYLIMIDAZOLE COMPOUNDS AS FUNGICIDES

The present invention relates to novel substituted phenylalkylimidazole compounds and their applications as agricultural or horticultural fungicides and as plant growth regulators.

In modern agriculture, high productivity is secured by means of fertilizers, agricultural chemicals and various agricultural materials. On the other hand, emergence of chemical-resistant bacteria due to continuous application of agricultural chemicals and diseases due to repeated cultivation of the same crop plants in a locally concentrated fashion, have now become serious problems. Further, the technique for regulating the growth of plants in a desirable direction is an extremely important technique from the viewpoint of the agricultural production and horticulture. Under these circumstances, it is strongly desired to develop highly safe novel agricultural and horticultural agents, and the present invention provides a means to meet such a desire.

According to the first aspect, the present invention provides a substituted phenylalkylimidazole compound of the formula:

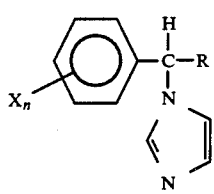

wherein R is an alkyl group or an alkenyl group, X is a halogen atom, a methyl group, a methoxy group, a phenoxy group, a trifluoromethyl group or a dimethylamino group, and n is an integer of 1 or 2.

According to the second aspect, the present invention provides an agricultural or horticultural fungicide comprising a compound of the formula (I) as an active ingredient.

According to the third aspect, the present invention provides a plant growth regulator comprising a compound of the formula (I) as an active ingredient.

Now, the present invention will be described in further detail with reference to the preferred embodiments.

The compound of the formula (I) can be prepared by the following method.

Namely, a compound of the following formula (II) is reacted with imidazole in a suitable solvent to obtain the desired compound:

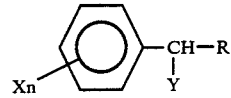

wherein R, X and n are as defined above with respect to the compound of the formula (I), and Y is a chlorine atom, a bromine atom or a lower alkylsulfonyloxy group.

The compound of the formula (II) can be prepared by a known reaction of the corresponding phenylalkylmethanol with thionyl chloride or a lower alkylsulfonic acid chloride.

The organic solvent to be used for the reaction includes, for example, benzene, toluene, xylene, monochlorobenzene, dichlorobenzene, dioxane, tetrahydrofuran, acetone, dimethylformamide, dimethylsulfoxide, acetonitrile and chloroform.

Imidazole is used in an excess amount. The reaction can efficiently be conducted in the presence of an alkali metal hydride or an alkali metal carbonate. The reaction may be conducted from 0 to 200° C. However, a temperature of not higher than 150° C. is preferred.

Now, representative compounds of the present invention will be shown in Table 1. For the sake of convenience, the structural formula in the Table is represented by substituents X and R only.

TABLE 1

| Compound No. | Substituent X | Substituent R | Melting point | IR spectrum (cm$^{-1}$) |
| --- | --- | --- | --- | --- |
| 1 | 4-CH$_3$ | n-C$_4$H$_9$ | oil | 3095, 1610, 910 |
| 2 | 2-CH$_3$ | n-C$_6$H$_{13}$ | oil | 3100, 1608, 910 |
| 3 | 3-CH$_3$ | n-C$_6$H$_{13}$ | oil | 3095, 1608, 909 |
| 4 | 4-CH$_3$ | n-C$_6$H$_{13}$ | oil | 3090, 900 |
| 5 | 4-Cl | —CH$_2$—C(CH$_3$)$_2$—CH$_3$ (with CH$_3$) | oil | 3100, 1598, 915 |
| 6 | 4-Cl | n-C$_3$H$_7$ | oil | 3080, 900 |
| 7 | 4-Cl | n-C$_4$H$_9$ | oil | 3095, 1595, 903 |
| 8 | 3-Cl | n-C$_5$H$_{11}$ | oil | 3100, 1600, 910 |
| 9 | 4-Cl | n-C$_5$H$_{11}$ | oil | 3100, 1599, 912 |
| 10 | 4-Cl | n-C$_6$H$_{13}$ | oil | 3080, 1590, 1485, 900 |
| 11 | 4-F | n-C$_6$H$_{13}$ | oil | 3100, 1600, 905 |
| 12 | 4-CH$_3$O | C$_2$H$_5$ | oil | 3100, 1610, 1510, 910 |
| 13 | 4-CH$_3$O | n-C$_4$H$_9$ | oil | 3100, 1610, 908 |
| 14 | 4-CH$_3$O | n-C$_6$H$_{13}$ | oil | 3095, 1613, 910 |
| 15 | 4-CF$_3$ | n-C$_6$H$_{13}$ | oil | 3100, 1621, 912 |
| 16 | 4-(CH$_3$)$_2$N | n-C$_4$H$_9$ | oil | 3090, 1612, 906 |
| 17 | 4-(CH$_3$)$_2$N | n-C$_6$H$_{13}$ | oil | 3100, 1615, 910 |
| 18 | 3-phenoxy | n-C$_6$H$_{13}$ | oil | 3090, 1580, 904 |
| 19 | 3,4-dichloro | n-C$_6$H$_{13}$ | oil | 3090, 1590, 1490, 910 |
| 20 | 4-Cl | i-C$_4$H$_9$ | oil | 3090, 1599, 916 |

TABLE 1-continued

| Compound No. | Substituent X | Substituent R | Melting point | IR spectrum (cm$^{-1}$) |
|---|---|---|---|---|
| 21 | 4-Cl | CH$_2$CH$_2$CH(CH$_3$)CH$_3$ | oil | 3100, 1600, 913 |
| 22 | 4-CF$_3$ | CH$_2$CH(CH$_3$)CH$_3$ | oil | 3090, 1619, 1495, 908 |
| 23 | 4-CH$_3$ | sec-C$_4$H$_9$ | oil | 3090, 1520, 910 |
| 24 | 4-CH$_3$ | i-C$_4$H$_9$ | oil | 3100, 1520, 915 |
| 25 | 2,4-Cl$_2$ | n-C$_3$H$_7$ | oil | 3098, 1593, 1563, 916 |
| 26 | 2,4-Cl$_2$ | n-C$_4$H$_9$ | oil | 3095, 1593, 1564, 914 |
| 27 | 2,4-Cl$_2$ | i-C$_4$H$_9$ | oil | 3097, 1594, 1563, 915 |
| 28 | 2,4-Cl$_2$ | n-C$_5$H$_{11}$ | oil | 3090, 1590, 1565, 910 |
| 29 | 2,4-Cl$_2$ | CH$_2$CH$_2$CH(CH$_3$)CH$_3$ | oil | 3100, 1595, 1565, 915 |
| 30 | 2,4-Cl$_2$ | CH$_2$CH(CH$_3$)CH$_2$CH$_3$ | oil | 3090, 1590, 1560, 910 |
| 31 | 2,4-Cl$_2$ | CH$_2$—C(CH$_3$)$_2$—CH$_3$ | oil | 3080, 1595, 1565, 915 |
| 32 | 2,4-Cl$_2$ | CH$_2$CH$_2$CH$_2$CH=CH$_2$ | oil | 3090, 3060, 1640, 1590, 1560, 916 |
| 33 | 2,4-Cl$_2$ | n-C$_6$H$_{13}$ | oil | 3090, 1593, 1565, 915 |
| 34 | 2,4-Cl$_2$ | CH$_2$-cyclopentyl | oil | 3090, 1590, 1565, 910 |
| 35 | 2,4-Cl$_2$ | CH$_2$CH$_2$CH=C(CH$_3$)$_2$ | oil | 3095, 1593, 1562, 910 |
| 36 | 2,4-Cl$_2$ | CH$_2$-cyclohexyl | oil | 3090, 1585, 1560, 909 |
| 37 | 2,4-Cl$_2$ | CH$_2$CH$_2$-cyclopentyl | oil | 3070, 1584, 1560, 905 |
| 38 | 2,4-Cl$_2$ | CH$_2$CH$_2$C(CH$_3$)$_2$CH$_3$ | oil | 3090, 1589, 1561, 907 |
| 39 | 2-Cl | n-C$_3$H$_7$ | oil | 3090, 1594, 1572, 910 |
| 40 | 2-Cl | n-C$_4$H$_9$ | oil | 3100, 1596, 1575, 912 |
| 41 | 2-Cl | n-C$_5$H$_{11}$ | oil | 3095, 1595, 1575, 912 |
| 42 | 2-Cl | n-C$_4$H$_9$ | oil | 3100, 1597, 1578, 918 |

Now, the present invention will be described in further detail with reference to Examples. However, it should be understood that the present invention is by no means restricted by such specific Examples.

PREPARATION EXAMPLE 1 (COMPOUND NO. 1)

4.0 g of imidazole was dissolved in 30 ml of dimethylformamide, and 1.4 g of sodium hydride (a 60% suspension in mineral oil) was gradually added thereto under stirring and cooling with ice. Further, 5.0 g of (4-methylphenyl)-1-chloropentane was added thereto at a temperature of not higher than 10° C. over a period of about 10 minutes.

The mixture was stirred for two hours while returning the temperature to room temperature and for three hours under heating at 50° C. Then, it was left to cool. The obtained mixture was poured into water, then extracted with ethyl acetate and treated with 40 ml of 1 N hydrochloric acid. Then, the obtained aqueous layer was turned to alkaline with an aqueous sodium hydroxide solution, whereupon the precipitated oily substance was extracted again with ethyl acetate.

This ethyl acetate layer was washed with water and dried over anhydrous sodium sulfate. Then, ethyl acetate was distilled off to obtain 1.2 g of desired 1-(4-methylphenyl)-1-(1H-imidazole-1-yl)pentane as a slightly yellow oily substance.

IR (neat): 3095, 1610, 910, (Cm$^{-1}$).

PREPARATION EXAMPLE 2 (COMPOUND NO. 7)

To a mixture comprising 5.2 g of imidazole, 10.5 9 of anhydrous potassium carbonate and 40 ml of dioxane, 5.5 g of 1-(4-chlorophenyl)-1-chloropentane was added over a period of about 30 minutes while stirring under reflax and further reacted for 8 hours under the same condition.

This reaction solution was left to cool, and then about 100 ml of water was added thereto. A precipitated oily substance was extracted with chloroform and treated with 3 N hydrochloric acid. The aqueous layer thereby obtained was turned to alkaline with an aqueous sodium hydroxide solution, whereupon a precipitated oily substance was extracted again with chloroform.

This chloroform layer was washed with water and dried over anhydrous sodium sulfate. Then, chloroform was distilled off to obtain 4.0 g of desired 1-(4-chlorophenyl)-1-(1H-imidazole-1-yl)pentane as a yellow oily substance.

IR (neat): 3095, 1595, 903, (cm$^{-1}$).

PREPARATION EXAMPLE 3 (COMPOUND NO. 32)

To a mixture comprising 1.2 g of imidazole, 0.24 g of 60% sodium hydride and 20 ml of dimethylformamide, 2.7 g of 1-(2,4-dichlorophenyl)-5-hexenyl ethanesulfonate was dropwise added while stirring at room temperature, and then the mixture was reacted for further 6 hours at 60° C. The reaction solution was poured into water, and a precipitated oily substance was extracted with dichloromethane, washed with water and dried over anhydrous sodium sulfate. Then, the solvent was distilled off to obtain a crude product.

This crude product was purified by silica gel column chromatography to obtain 1 g of the desired product as an oily substance.

IR (neat): 3090, 3060, 1640, 1590, 1560, 916.

For the application of the compound of the present invention, it may be formulated into a wettable powder, an emulsifiable concentrate, a granule, a dust, etc. by means of a solid carrier or a liquid carrier in accordance with a usual agricultural formulation method.

As the liquid diluent or carrier, an aromatic hydrocarbon such as xylene, a chlorinated aromatic hydrocarbon such as chlorobenzene, an alcohol such as butanol, a ketone such as methyl isobutyl ketone or isophorone, or a polar solvent such as dimethyl formamide or dimethyl sulfoxide, and water, are preferably employed.

As the solid diluent or carrier, a mineral powder such as kaolin, talc, clay, montmorillonite or diatomaceous earth, or a synthetic or natural polymer compound such as a polyalkylene glycol ester gum, may be employed.

Preferred emulsifiers include, for example, non-ionic emulsifiers such as polyoxyethylene fatty acid esters and polyoxyethylene alkylethers, and anionic emulsifiers such as alkylaryl sulfonates, aryl sulfonates and alkyl sulfonates. Preferred dispersants include, for example, lignin and methyl cellulose.

Extenders such as carboxymethyl cellulose as well as powdery, granular or grating natural and synthetic polymers such as gum Arabic, polyvinyl alcohol and polyvinyl acetate, may be used for the formulations.

The formulations usually contain from 0.1 to 95% by weight, preferably from 0.5 to 50% by weight, of the active compound.

The fungicide and the plant growth regulator of the present invention are applied in sufficient amounts so that the active compounds provide adequate effects. The dose of the active ingredient is within a range of from 50 to 2,000 g/ha, usually from 50 to 1,000 g/ha.

Now, the present invention will be described with reference to Formulation Examples. In these Examples, "parts" means "parts by weight".

| Formulation Example 1 | |
|---|---|
| Compound No. 1 | 10 parts |
| Clay | 80 parts |
| Polyoxyalkylphenyl sulfate | 5 parts |
| White carbon (fine silica) | 5 parts |

The above materials were pulverized and mixed to obtain a wettable powder.

| Formulation Example 2 | |
|---|---|
| Compound No. 3 | 20 parts |
| Xylene | 70 parts |
| Sorpol 800 A (trademark of Toho Chemical Co., Ltd. for a surfactant comprising a polyoxyethylene sorbitan alkylate, a polyoxyethylene alkylphenol polymer and calcium sulfonate, manufactured by Toho Chemical Co., Ltd.) | 10 parts |

The above materials were mixed to obtain an emulsifiable concentrate.

| Formulation Example 3 | |
|---|---|
| Compound No. 5 | 10 parts |
| Lignin | 2 parts |
| Bentonite | 88 parts |

The above materials were mixed and kneaded with water, followed by granulation and drying to obtain a granule.

| Formulation Example 4 | |
|---|---|
| Compound No. 16 | 20 parts |
| Isophorone | 20 parts |
| Xylene | 20 parts |
| Orthochlorotoluene | 35 parts |
| Sorpol 900 A (trade mark of Toho Chemical Co., Ltd. for a surfactant comprising a polyoxyethylene sorbitan alkylate, a polyoxyethylene alkylphenol polymer, a polyoxyethylene alkylallylether, and calcium sulfonate, manufactured by Toho Chemical Co., Ltd.) | 7.5 parts |
| Sorpol 900 B (trade mark of Toho Chemical Co., Ltd. for a surfactant comprising a polyoxyethylene sorbitan alkylate, a polyoxyethylene alkylphenol polymer, a polyoxyethylene alkylallylether, and calcium sulfonate, manufactured by Toho Chemical Co., Ltd.) | 7.5 parts |

The above material were mixed to obtain an emulsifiable concentrate.

Now, mycelium growth inhibitory effects and disease preventive effects of the compounds of the present invention against typical fungi will be described with respect to Test Examples.

TEST EXAMPLE 1

Test for mycelium growth inhibitory effects on a Petri dish

A potato-dextrose agar culture medium (PDA medium) and a dimethyl sulfoxide solution of the compound are mixed to a concentration of 100 ppm, and the mixture was poured into a Petri dish to form a plate culture medium. Onto this culture medium, two disc specimens with a diameter of 4 mm of each of *Pythium graminicola*, *Fusarium oxysporum* and *Rhizoctonia solani*, which were preliminarily cultured on PDA culture media, were placed, and cultured at 25° C. for two days in the case of *Pythium graminicola*, five days in the case of *Fusarium oxysporum* and for three days in the case of *Rhizoctonia solani*. Then, the diameter of each colony was measured and compared with the colony diameter on a non-treated medium, and the growth inhibition was calculated in accordance with the following equation.

$$\text{Growth inhibition (\%)} = \frac{A - B}{A} \times 100$$

A: Colony diameter on the non-treated medium
B: Colony diameter on the treated medium The average values of the results are shown in Table 2.

TABLE 2

| Compound No. | Fungi | | |
|---|---|---|---|
| | Pythium graminicola | Fusarium oxysporum | Rhizoctania solani |
| 1 | 100 | 98 | 98 |
| 2 | 100 | 98 | 100 |
| 3 | 100 | 98 | 100 |
| 4 | 100 | 98 | 100 |
| 5 | 100 | 98 | 100 |
| 6 | 100 | 98 | 100 |
| 7 | 100 | 98 | 98 |
| 8 | 100 | 98 | 98 |
| 9 | 100 | 98 | 100 |
| 10 | 100 | 98 | 100 |
| 11 | 100 | 98 | 100 |
| 12 | 100 | 98 | 98 |
| 13 | 100 | 98 | 98 |
| 14 | 100 | 98 | 98 |
| 15 | 100 | 100 | 100 |
| 16 | 100 | 98 | 98 |
| 17 | 100 | 98 | 98 |
| 18 | 98 | 98 | 98 |
| 19 | 98 | 98 | 100 |
| 20 | 100 | 100 | 100 |
| 21 | 100 | 100 | 100 |
| 22 | 98 | 100 | 100 |
| 23 | 98 | 100 | 100 |
| 24 | 100 | 100 | 100 |
| 25 | 100 | 100 | 100 |
| 26 | 100 | 98 | 100 |
| 27 | 100 | 98 | 98 |
| 28 | 100 | 100 | 100 |
| 29 | 100 | 100 | 100 |
| 30 | 100 | 100 | 100 |
| 31 | 100 | 100 | 100 |
| 32 | 100 | 100 | 100 |
| 33 | 98 | 98 | 100 |
| 34 | 100 | 100 | 100 |
| 35 | 100 | 100 | 100 |
| 36 | 100 | 100 | 100 |
| 38 | 100 | 100 | 100 |
| 39 | 100 | 100 | 100 |
| 40 | 100 | 100 | 100 |
| 41 | 100 | 100 | 100 |
| 42 | 100 | 100 | 100 |

TEST EXAMPLE 2

Test for mycelium growth inhibitory effects on a Petri dish

A PDA medium and a dimethyl sulfoxide solution of the compound were mixed to a concentration of 100 ppm, and the mixture was poured into a Petri dish to form a plate culture medium. Onto this culture medium, two disc specimens with a diameter of 4 mm of each of *Botrytis cinerea*, *Pseudocercosporella herpotrichides* and *Pyricularia oryzae*, which were preriminarily cultured on PDA culture media, were placed and cultured at 25° C. for two days in the case of *Botrytis cinerea*, at 20° C. for ten days in the case of *Pseudocercosporella herpotrichides* and at 25° C. for 5 days in the case of *Pyricularia oryzae*. Then, the diameter of each colony was measured and compared with the colony diameter on a non-treated medium, and the growth inhibition was calculated in the same manner as in Test Example 1. The average values of the results are shown in Table 3.

TABLE 3

| Compound No. | Fungi | | |
|---|---|---|---|
| | Botrytis cinerea | Pseudocercosporella herpotrichides | Pyricularia oryzae |
| 5 | 98 | 98 | 100 |
| 6 | 98 | 98 | 98 |
| 9 | 98 | 98 | 98 |
| 22 | 98 | 98 | 100 |
| 23 | 100 | 100 | 100 |
| 25 | 100 | 100 | 100 |
| 26 | 100 | 100 | 100 |
| 27 | 100 | 100 | 98 |
| 28 | 100 | 100 | 98 |
| 30 | 98 | 100 | 98 |
| 32 | 100 | 100 | 100 |
| 33 | 100 | 98 | 98 |
| 34 | 100 | 100 | 100 |
| 35 | 100 | 100 | 100 |
| 36 | 100 | 100 | 100 |
| 37 | 100 | 100 | 100 |
| 38 | 100 | 100 | 100 |
| 39 | 100 | 100 | 100 |
| 40 | 100 | 100 | 100 |
| 41 | 100 | 100 | 100 |
| 42 | 100 | 100 | 100 |

TEST EXAMPLE 3

Test for preventive effects against downy mildew of cucumber

Cucumber (variety: Kashu No.1) was cultured in a porous porcelain pot having a diameter of 9 cm, and when it reached a 3-leaf stage, each test compound was formulated in accordance with Formulation Example 1 to have a concentration of 50 ppm, and 10 ml of the solution of the test compound was sprayed by means of a spray gun. Three cucumber plants were treated with each test compound.

After drying them 24 hours, a suspension of spores ($2 \times 10^5$ spores/ml) of *Pseudoperonosporea cubensis* causing downy mildew of cucumber, was sprayed and inoculated to each plant. After the inoculation, the cucumber plants were cultured at 20° C. under a moisture-saturated condition for 12 hours and then at 20° C. under a relative humidity of from 70 to 80% for 6 days. Seven days after the inoculation, the proportions of lesion on the first leaf and the second leaf were examined, and the control value were determined by the following formula to obtain the results as shown in Table 4.

$$\text{Control value} = \frac{C - D}{C} \times 100$$

C: Proportion of lesion at the non-treated section
D: Proportion of lesion at the treated section

TABLE 4

| Compound No. | Control value | Compound No. | Control value | Compound No. | Control value |
|---|---|---|---|---|---|
| 1 | 100 | 13 | 100 | 30 | 100 |
| 2 | 100 | 16 | 100 | 31 | 100 |
| 3 | 100 | 17 | 100 | 34 | 100 |
| 4 | 100 | 19 | 98 | 36 | 100 |
| 10 | 100 | 22 | 100 | 37 | 100 |
| 12 | 100 | 25 | 100 | 38 | 100 |

TEST EXAMPLE 4

Test for preventive effects against powdery mildew of wheat

Wheat (variety: Norin No. 61) was cultured in a pot having a diameter of 9 cm, and when it reached a 2-leaf stage, each test compound was formulated in accordance with Formulation Example 4 to have a concentration of 50 ppm, and 20 ml of the solution of the test compound was sprayed by means of a spray gun. With respect to each test compound, treatment was conducted in two series each consisting of 13 wheat plants per section.

After drying the plants for 24 hours, conidia of Eryshiphe graminis causing powdery mildew of wheat, were sprayed and inoculated to each wheat plant. After this inoculation, the wheat plants were cultured at 20° C. in a dark place under a moisture-saturated condition for 12 hours and then at 20° C. for 6 days. Seven days after inoculation, the portions of lesion on the first leaf and the second leaf were examined, and the control value was obtained in the same manner as in Test Example 3 to obtain the results as shown in Table 5.

TABLE 5

| Compound No. | Control value | Compound No. | Control value | Compound No. | Control value |
|---|---|---|---|---|---|
| 1 | 100 | 16 | 100 | 28 | 100 |
| 2 | 100 | 17 | 100 | 30 | 100 |
| 3 | 100 | 18 | 100 | 31 | 100 |
| 5 | 100 | 19 | 98 | 32 | 100 |
| 6 | 100 | 20 | 100 | 34 | 100 |
| 7 | 100 | 21 | 100 | 35 | 100 |
| 9 | 100 | 22 | 100 | 37 | 100 |
| 10 | 100 | 24 | 100 | 38 | 100 |
| 11 | 100 | 27 | 100 | | |

TEST EXAMPLE 5

Test for preventive effects against powdery mildew of cucumber

Cucumber (variety: Sagami Hanjiro) was cultured in a porous porcelain pot having a diameter of 9 cm, and when it reached a 2-leaf stage, each test compound was formulated in accordance with Formulation Example 1 to have a concentration of 100 ppm, and 10 ml of the solution of the test compound was sprayed by means of a spray gun. Three cucumber plants were treated by each test compound.

After drying them for 24 hours, a suspension of spores ($1 \times 10^5$ spores/ml) of Sphaerotheca fuliginea causing powdery mildew of cucumber, was sprayed and inoculated to each plant. After this inoculation, the cucumber plants were cultured at 28° C. for 12 hours, in a moisture-saturated condition and then at 28° C. for 7 days. 8 days after the inoculation, the proportions of lesion on the first leaf and the second leaf were examined, and the control value was determined in the same manner in the Test Example 3 to obtain in the results as shown in Table 6.

TABLE 6

| Compound No. | Control value |
|---|---|
| 5 | 100 |
| 18 | 100 |
| 21 | 100 |
| 31 | 100 |

TEST EXAMPLE 6

Test for inhibition of elongation of rice seedling leaf sheath

Seeds of rice (Koshihikari) were sterilized and then immersed in water at 28° C. for 48 hours for germination. A filter paper was put in a Petri dish having a diameter of 6 cm, and 10 ml of Hogland water culture solution having a predetermined amount of the sample compound dissolved therein, was added. Then, ten germinated rice seeds were sown and cultured at 28° C. for 7 days under continuous irradiation with about 5,000 lux. Then, the length of the second leaf sheath was measured. The obtained second leaf sheath length was divided by the length of the non-treated second leaf sheath to obtain a leaf sheath elongation rate. The results are shown in Table 7.

TABLE 7

| Compound No. | Concentration (ppm) | Leaf sheath elongation rate (%) |
|---|---|---|
| 1 | 10 | 11 |
|   | 3  | 20 |
|   | 1  | 69 |
| 2 | 10 | 7  |
|   | 3  | 32 |
|   | 1  | 63 |
| 3 | 10 | 28 |
|   | 3  | 52 |
|   | 1  | 79 |
| 4 | 10 | 14 |
|   | 3  | 58 |
|   | 1  | 79 |
| 5 | 10 | 32 |
|   | 3  | 63 |
|   | 1  | 78 |
| 6 | 10 | 10 |
|   | 3  | 68 |
|   | 1  | 74 |
| 7 | 10 | 16 |
|   | 3  | 44 |
|   | 1  | 80 |
| 8 | 10 | 15 |
|   | 3  | 57 |
|   | 1  | 85 |
| 9 | 10 | 18 |
|   | 3  | 65 |

TABLE 7-continued

| Compound No. | Concentration (ppm) | Leaf sheath elongation rate (%) |
|---|---|---|
|  | 1 | 82 |
| 10 | 10 | 42 |
|  | 3 | 75 |
|  | 1 | 83 |
| No treatment | 0 | 100 |
| 11 | 10 | 41 |
|  | 3 | 55 |
|  | 1 | 76 |
| 21 | 10 | 55 |
|  | 3 | 75 |
|  | 1 | 92 |
| 22 | 10 | 51 |
|  | 3 | 71 |
|  | 1 | 84 |
| 23 | 10 | 37 |
|  | 3 | 58 |
|  | 1 | 74 |
| 24 | 10 | 67 |
|  | 3 | 48 |
|  | 1 | 83 |
| 25 | 10 | 52 |
|  | 3 | 63 |
|  | 1 | 71 |
| 26 | 10 | 46 |
|  | 3 | 71 |
|  | 1 | 81 |
| 27 | 10 | 58 |
|  | 3 | 71 |
|  | 1 | 80 |
| 31 | 10 | 72 |
|  | 3 | 82 |
|  | 1 | 90 |
| No treatment | 0 | 100 |

TEST EXAMPLE 7

Test for inhibition of elongation of cucumber seedlings

Into a Petri dish having a diameter of 6 cm with a filter paper put therein, 5 ml of a Hogland water culture solution having a predetermined amount of the test compound dissolved therein, was added. Then, five germinated seeds were sown and cultured at 28° C. for 7 days under continuous irradiation with about 5,000 lux. Then the length of hypocotyl was measured. The obtained length of the hypocotyl was divided by the length of the non-treated hypocotyl to obtain in a hypocotyl elongation rate. The results are shown in Table 8.

TABLE 8

| Compound No. | Concentration (ppm) | Hypocotyl elongation rate (%) |
|---|---|---|
| 1 | 10 | 41 |
|  | 3 | 64 |
|  | 1 | 88 |
| 2 | 10 | 40 |
|  | 3 | 57 |
|  | 1 | 92 |
| 3 | 10 | 37 |
|  | 3 | 55 |
|  | 1 | 78 |
| 4 | 10 | 48 |
|  | 3 | 75 |
|  | 1 | 97 |
| 5 | 10 | 31 |
|  | 3 | 47 |
|  | 1 | 66 |
| 6 | 10 | 41 |
|  | 3 | 55 |
|  | 1 | 88 |
| 7 | 10 | 34 |
|  | 3 | 61 |
|  | 1 | 78 |
| 8 | 10 | 36 |
|  | 3 | 47 |
|  | 1 | 81 |
| 9 | 10 | 32 |
|  | 3 | 50 |
|  | 1 | 84 |
| 10 | 10 | 50 |
|  | 3 | 70 |
|  | 1 | 102 |
| No treatment | 0 | 100 |
| 20 | 10 | 46 |
|  | 3 | 60 |
|  | 1 | 75 |
| 21 | 10 | 52 |
|  | 3 | 67 |
|  | 1 | 79 |
| 22 | 10 | 54 |
|  | 3 | 78 |
|  | 1 | 95 |
| 23 | 10 | 41 |
|  | 3 | 65 |
|  | 1 | 83 |
| 24 | 10 | 56 |
|  | 3 | 66 |
|  | 1 | 89 |
| 25 | 10 | 38 |
|  | 3 | 74 |
|  | 1 | 79 |
| 27 | 10 | 42 |
|  | 3 | 67 |
|  | 1 | 89 |
| No treatment | 0 | 100 |

As described in the foregoing, the present invention exhibits fungicidal activities against various filamental fungi, shows preventive effects against diseases of crop plants and has specific plant growth regulating activities, and thus it presents an effective means for improving the yield of harvest without phytotoxicity.

We claim:

1. A substituted phenylalkylimidazole compound of the formula:

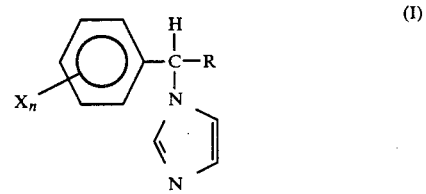

wherein R is an alkyl group having three or more carbon atoms or an alkenyl group, X is a halogen atom, a methyl group, a methoxy group, a phenoxy group, a trifluoromethyl group or a dimethylamino group, and n is an integer of 1 or 2.

2. An agricultural or horticultural fungicide comprising a compound of the formula (I) as defined in claim 1, as an active ingredient.

3. A plant growth regulator comprising a compound of the formula (I) as defined in claim 1, as an active ingredient.

* * * * *